US006299632B1

(12) United States Patent
Jaillet

(10) Patent No.: US 6,299,632 B1
(45) Date of Patent: Oct. 9, 2001

(54) METHOD FOR CHANGING CRITICAL BRAIN ACTIVITY USING LIGHT AND SOUND

(76) Inventor: Peter Jaillet, 4212 Harvest Hill Ct., Carrollton, TX (US) 75010

( * ) Notice: Subject to any disclaimer, the term of this patent is extended or adjusted under 35 U.S.C. 154(b) by 0 days.

(21) Appl. No.: 09/201,093

(22) Filed: Nov. 30, 1998

(51) Int. Cl.[7] ................................................. A61N 5/06
(52) U.S. Cl. ............................... 607/88; 600/27; 128/898
(58) Field of Search .................. 600/26, 27, 28, 600/544, 545; 607/88, 90, 91

(56) References Cited

U.S. PATENT DOCUMENTS

| | | | |
|---|---|---|---|
| 5,036,858 | 8/1991 | Carter et al. ........................ 128/732 |
| 5,365,939 | 11/1994 | Ochs ................................... 128/732 |
| 5,409,445 | * 4/1995 | Rubins ................................. 600/27 |
| 5,562,719 | * 10/1996 | Lopez-Claros ....................... 607/88 |
| 5,899,867 | * 5/1999 | Collura ............................... 600/545 |

* cited by examiner

Primary Examiner—Linda C. M. Dvorak
Assistant Examiner—R. Kearney
(74) Attorney, Agent, or Firm—Gardere Wynne Sewell LLP; Edwin S. Flores; Sanford E. Warren, Jr.

(57) ABSTRACT

An apparatus and method for selectively stimulating cortical brain activity of the non-dominant hemisphere using light and/or sound comprising a surface (11) placed in close proximity to a patient's eyes (20,30) and a plurality of lights (12) disposed on the surface (11) wherein the plurality of lights (12) selectively stimulate the non-dominant eye (30) connected to the non-dominant cerebral hemisphere, as disclosed.

18 Claims, 2 Drawing Sheets

METHOD FOR CHANGING CRITICAL BRAIN ACTIVITY USING LIGHT AND SOUND

TECHNICAL FIELD OF THE INVENTION

The present invention relates in general to the field of critical brain stimulation and, more particularly, to an apparatus and method for increasing learning and athletic potential by changing and controlling critical brain activity of the non-dominant cerebral hemisphere greater than the dominant cerebral hemisphere through the use of light and/or sound.

BACKGROUND OF THE INVENTION

Without limiting the scope of the invention, its background is described in connection with the use of light therapy to stimulate cerebral hemispheres, as an example.

Light has been shown to effect the stability of a person's energy, mood, sleep, concentration and the regulation of a person's circadian rhythms. Light deprivation, for example, has been shown to cause fatigue, irritability, anxiety, weight gain, social withdrawal and a lack of alertness.

The human brain produces detectable signals that vary in strength and frequency over time. These signals are detectable as electromagnetic waves, and vary from one part of the brain to another and may, in fact, vary over time. Electromagnetic waves with different frequencies are associated with different moods and mental abilities. For example, a brain frequency of 13 Hertz or higher is known as a "beta rhythm" and is normally associated with daylight activity when all five sensory organs are functioning. In contrast, a brain wave with a frequency of 8–13 Hertz is known as a "alpha rhythm" and is often associated with a relaxed creative state. Brain waves known as "theta rhythm" and "delta rhythm" have frequencies of 4–8 Hertz and 0.5–4 Hertz, respectively. Theta-rhythm abnormalities have been associated with learning disorders in adolescents. The delta-rhythm is generally found in normal sleep.

It is generally believed that a person afflicted with a sleeping disorder has problems generating a delta rhythm. In contrast, people who have difficulties learning or display behavioral problems that affect learning, have problems associated with abnormalities of the alpha rhythm. These rhythms have been found to be regulated by brain biochemistry.

Two biochemical compounds have been implicated in the control of brain patterns and rhythms: melatonin and serotonin. Melatonin is a metabolite of serotonin, and is synthesized by the pineal gland. The production of melatonin from the pineal gland is stimulated by the sympathetic neural output of the supra chiasmatic nuclei. Production of melatonin serves as an internal body clock that is regulated by the light-dark cycle, as sensed by the visual system. As light enters the eye, the reticulo-hypothalmic tract synchronizes the suprachiasmatic nuclei using biochemical neurotransmitters such as melatonin. Attempts at changing brain biochemistry however, are greatly limited by the side-effects exhibited by most therapeutic drug regimens.

The use of light therapy, unlike drug therapy, has been used to treat patients that have been afflicted with a seasonal affective disorder. U.S. Pat. No. 5,562,719 to Lopez-Claros describes one such method for treating seasonal affective disorders that relies on preferential light stimulation in a hemifield pattern only affecting one quadrant or 50% of the non-dominant cerebral hemisphere. Seasonal affective disorder is a condition that affects from 5–20% of the population in areas with decreased year time light levels, such as the Northern Hemisphere. A common treatment for seasonal affective disorders is the use of lamps or light boxes that provide between 2,500 to 10,000 lux illumination in a hemifield pattern only affecting the inferior quadrant or 50% of the non-dominant cerebral hemisphere. This level illumination is an attempt to stimulate summer-like light levels. The Lopez-Claros patent is directed to the stimulation of one cerebral hemisphere to a greater degree than the other, thereby treating seasonal affective disorder by preferential light treatment. The Lopez-Claros invention, however, stimulates only one quadrant of the optical axis or 50% in both eyes thereby precluding its use in the stimulation of a hemisphere wholely.

As apparatus and method for treating an individual by electroencephalographic disentrainment feedback is the focus of U.S. Pat. No. 5,365,939 issued to Ochs. Electroencephalographic disentrainment feedback involves measuring a patient's brain waves, and based on those brain waves, generating impulses that disrupt brain waves by "disentraining" brain waves that are "entrained" or entrenched in the brain. By "disentraining" the entrenched brain waves, a patient's sub-optimal post-traumatic neural functioning is restored. The apparatus, however, requires the supervision of a doctor, as people with hypersensitivity may require that treatment be immediately stopped. The increased supervision makes the cost of use very great and eliminates its portability.

A slight variation from the Ochs patent, is U.S. Pat. No. 5,036,858 issued to Carter and Russell, that involves using two frequencies, with a slight frequency differential between the two frequencies, to change a patient's brain waves. In this patent, the patient's brain waves are also measured, and based on these measurements, disruptive brain impulses are generated that disrupt the patient's brain waves in a constant feedback mechanism.

What is needed is a simplified apparatus and method that enhances the innate abilities of individuals with learning disorders. The apparatus and method must also be simple to use, inexpensive and portable, in order to provide for greater distribution to those most in need of enhanced learning abilities. Individuals who would benefit the most from an inexpensive, simple to use device that increases learning abilities are the poor in urban inner cities and in rural areas. More specifically, what is needed is a simple, inexpensive device that can be used by elementary and secondary school children whose parent, or guardian, can ill afford expensive drug or light treatments requiring medical supervision. Others that would benefit from such an apparatus and method are athletes, business people, and academicians.

SUMMARY OF THE INVENTION

The present invention disclosed herein is an apparatus for selectively stimulating a non-dominant cerebral hemisphere greater than the dominant cerebral hemisphere to create a balance of integration of excitatory post synaptic potentials (EPSP). The apparatus for selectively stimulating the non-dominant cerebral hemisphere greater than the dominant cerebral hemisphere comprises a surface placed in close proximity to a patient's eyes and a plurality of lights disposed on the surface. The plurality of lights stimulate the eye connected to the non-dominant cerebral hemisphere greater than the dominant cerebral hemisphere at a rate of approximately 60/40. This occurs in order to increase a patient's ability to maintain a heighten mental status, and in turn sets up for a globality of increased muscular activity.

In one embodiment the apparatus of the present invention is a device that covers the patient's eyes, such as a pair of sunglasses. Other devices may utilize similar technology in order to enhance ones ability to mentally focus. These devices include sports helmets that are used to protect players' craniums and may be integrated into the protective head gear, i.e., football, hockey, baseball, racing car, motorcycle and bicycle helmets.

Another application of the technology is with computer monitors and televisions. This would encompass either an oscillating or plurality of lights set up in a prescribed manner on a person's computer monitor. The light pattern of the present invention could be displayed in a subliminal alternating checkerboard pattern that would be set to the individual user. This will stimulate the non-dominant cerebral hemisphere greater than the dominant cerebral hemisphere.

Alternatively, the surface may be sleeping goggles. In yet another embodiment of the present invention glasses, such as a monocle, that reflect light from a source next to the eye is reflected from the glass surface are encompassed by the examples.

The types of light that are used with the apparatus and method of the present invention include white light, plane polarized light, or light that varies in color. The timing and intensity of the light may be controlled by a microprocessor or by an operator.

BRIEF DESCRIPTION OF THE DRAWINGS

For a more complete understanding of the features and advantages of the present invention, reference is now made to the detailed description of the invention along with the accompanying drawing in which corresponding numerals in the different figures refer to corresponding parts and, in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Figure 1:
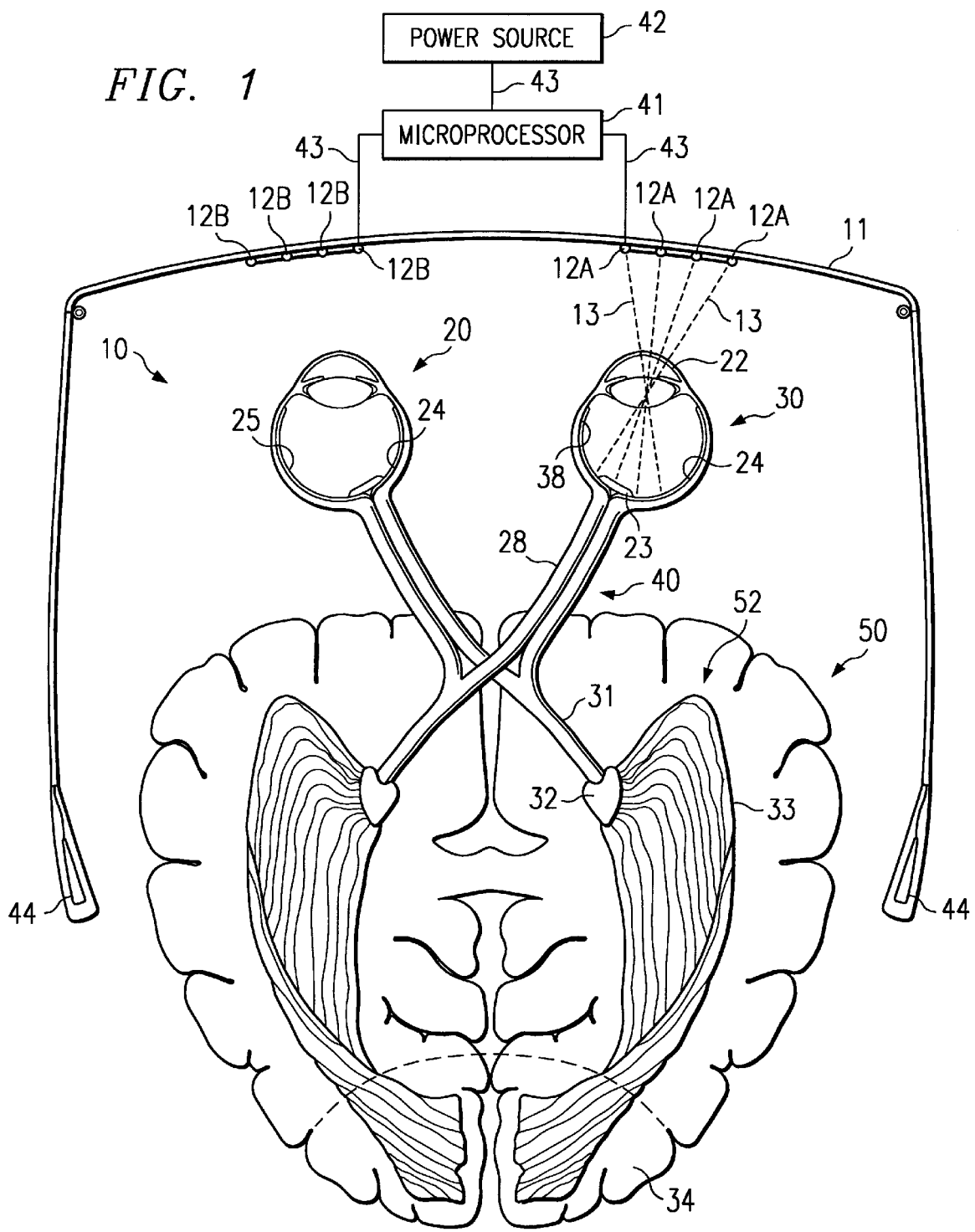
FIG. 1 is a presentation of the neural anatomy of the optical system and the relation of the visual fields.

In FIG. 1, a representation of the neurological anatomy of the optical system is generally depicted as 10. Generally depicted is an eye 20 associated and controlled by the dominant cerebral hemisphere. Also depicted, is a non-dominant eye 30 associated with, and connected to, the non-dominant cerebral hemisphere. Dominant eye 20 and non-dominant eye 30 are connected via nerves 40 to the brain 50. A surface 11 is in close proximity to the dominant eye 20 and the non-dominant eye 30. The non-dominant eye 30 is stimulated by lights 12A on the surface 11 that serve to stimulate the nondominant eye 30 at a greater intensity than lights 12B that stimulate the dominant eye.

The surface 11 may be, for example, a planar or concave surface, such as sunglasses in this particular description, compared to other previously mentioned applications. The surface 11 is fitted with a plurality of lights 12, or using a source that can carry light such as fiber optics. In one embodiment the number of lights 12 associated with each eye is four. The number of lights may be greater depending on the needs of the patient. The lights 12 are mounted on, or integral to, the surface 11. The lights 12 may be, for example, white light, multicolored light, or plane polarized light. If the lights are multicolored, they may be primary colors or a combination of primary colors to achieve other color combinations. The lights 12 may be turned on and off by a self-contained microprocessor 41. Alternatively, the frequency and intensity of the light 13 produced by the lights 12 may be independently powered and controlled by an operator.

The lights 12 and microprocessor 41 may be an integral part of the surface 11 and may have a self-contained power source 42. The self-contained power source 42 may be, for example, a small battery or may use a solar powered source. Alternatively, the power source 12 maybe electrically connected to the microprocessor 41 and the surface 11 via wires 43.

In operation, light 13 passes through the pupil 22 of the non-dominant eye 30 and stimulates the rods and cones 24 located in the retina 25 of the non-dominant eye 30. Light 13 is reflected on each of the four known quadrants of the retina 25 depending on which light 12A is activated. By projecting the light 13 on all four quadrants of the retina 25, the light 13 and the images created on those visual fields are projected onto the retina 25 upside down and in reverse. The signal produced by the rods and cones 24 activates ganglion cell axons 27 that carry visual information from the four quadrants on the retina 25. The nervous pulses traveling through the ganglion cell axons 27 converge toward the optic disk 23 in an orderly fashion, in order to maintain approximately the same relation to each other as they reach the optic disk 22. The visual signal is then passed along the optic nerve 28 onto the optic tract 31. The visual signal synapses into the lateral geniculate body 32 allowing cortical radiations 33 to travel back to the occipital lobe 34 before ascending to the cortical motor strip in the frontal lobe of the brain. The dominant eye is stimulated by lights 12B in the same manner, but to a lesser extent.

The apparatus and method of the present invention may be practiced using a variety of illumination intensities. In addition to different illumination intensities, different patterns and frequencies of lighting may be used to stimulate the four quadrants of the retina 25 in different manners, depending on the needs of the individual patient. It is found through examination that there are particular frequencies that are more suitable to different individuals. As well as the intensities of the light depending on ones ability to see and perceive the light. Those having very large physiological blind spots may require a greater intensity of light."

Figure 2:
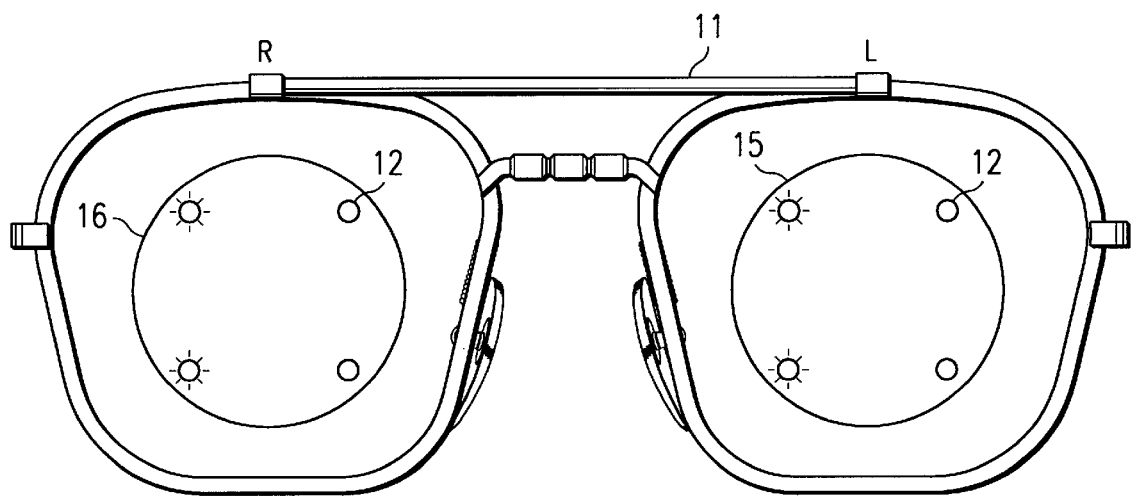
FIG. 2 is a schematic representation of the optical stimulant of the present invention.

FIG. 2 depicts a schematic representation of an apparatus for providing light 13 to the four quadrants of the retina 25 in order to stimulate the non-dominant cerebral hemisphere greater than the dominant cerebral hemisphere. Depicted in FIG. 2 is a surface 11, in this case, on the form of sunglasses that permit little or no light to pass through the lenses. While sunglasses are depicted, it will be understood to one skilled in the art that optical or transparent glasses that allow modified or normal light to pass through may be used. In an alternative embodiment, the glasses may be transparent, but the patient may be placed in a darkened room. Alternatively, the surface 11 may also be a monocle or an eye-patch that exclusively covers only the non-dominant eye 30. In yet another embodiment, surface 11 is a reflective surface that reflects light 13 from a light source that is not integral to the surface 11. In this embodiment, light 13 is bounced off the surface 11 onto the retina 25.

The surface 11 is depicted as having a right circle 15 and a left circle 16. Spaced evenly in each of the right circle 15 and the left circle 16 are lights 12. The lights 12 are disposed generally equidistant in the right and left circles 15, 16. The lights 12 are positioned to selectively stimulate each of the four quadrants of the retina 25.

Concomitant with, or exclusive of, the light source, sound may be selectively provided to the ear connected to the non-dominant cerebral hemisphere by a sound source that selectively provides sound to the ear connected to the non-dominant cerebral hemisphere. In most cases sound is provided to the ear that is contralateral or opposite the eye associated with the non-dominant cerebral hemisphere that is being stimulated. The choice of sides is determined by the physician or other qualified person fitting the patient. In most cases the dominant ear needs no additional stimulation. The non-dominant ear will be the side that is stimulated bringing the non-dominant side up to a level more equal to the dominant side. In one embodiment the sound source may be part of a headset. In yet another embodiment, the headset is connected to the surface having the plurality of lights.

Another embodiment of the present invention is an apparatus for treating learning disorders by selectively stimulating the non-dominant cerebral hemisphere greater than the dominant cerebral comprising, a surface placed in close proximity to a patient's eyes, a plurality of lights disposed on the surface, a microprocessor for controlling the lights, the plurality of lights controlled by the microprocessor, wherein only the lights in front of the non-dominant hemisphere are activated, and a power source that provides electricity to the lights and the microprocessor.

The present invention provides a method for selectively stimulating the non-dominant cerebral hemisphere greater than the dominant cerebral hemisphere comprising the steps of, identifying the non-dominant hemisphere of a patient and selectively stimulating the non-dominant visual cortex of the patient greater than the dominant visual cortex using light.

In this invention a multiplicity of lights are used to stimulate the four quadrants. The quadrants consist of a Nasal superior and inferior quadrant, and a Temporal superior and inferior quadrant. In the preferred embodiment four lights are employed with each eye. However the number of lights employed can vary based on the needs of the patient.

Figure 3:
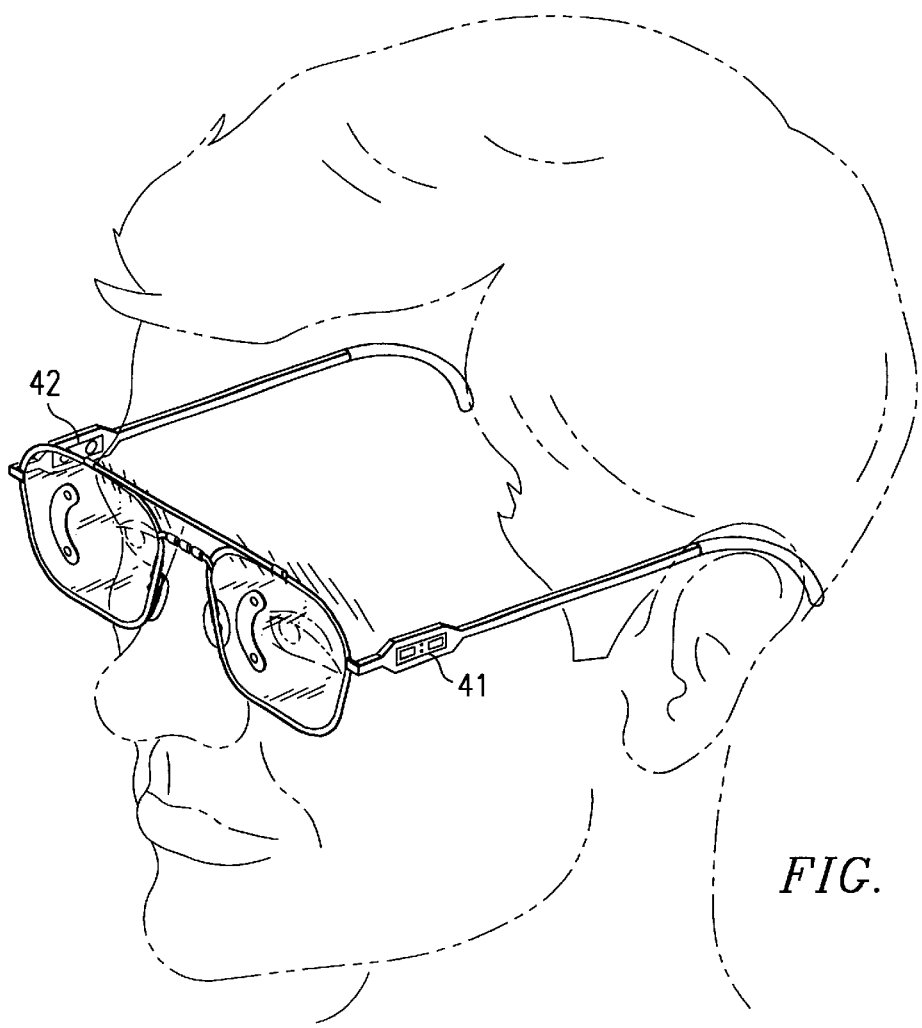
FIG. 3 is a schematic representation of the optical stimulant in a hemifield pattern.

In an alternative embodiment, illustrated in FIG. 3, hemifield stimulation is employed. In this embodiment specific quadrants are excited. In this embodiment two lights may be associated with each eye. The lights of one eye e.g., the right eye would be focused on the temporal aspects of the patients eye. This stimulates the nasal or medial aspect of the eye the superior and inferior quadrant rods and cones of the retina. Once in the retina it excites the ganglion cells before passing through the optic nerve. It then decussates through the optic chaism to pass on to the next relay that is the lateral geniculate, before finally passing to the occipital lobe Area 19 in the calcarine sulcus. The left set of lights are on the medial or nasal aspects of the patients left eye, this stimulates the temporal fibers, superior and inferior latertal quadrant. It follows through the same pathway as above before ending in the calcarine sulcus in the occipital lobe area 19. In this pattern the lights are focussed in the inferior and superior quadrants on either the right or the left side of each eye. The neurological pathways used, will be the same as previously mentioned only the input will go to the side of the brain opposite the layout of the lights,i.e., lights on the right side (temporal) of the right eye and the right side (nasal) of the left eye will stimulate the left side of the brain.

An alternative embodiment of the present invention is the specific stimulation of the non-dominant auditory neurological pathway to stimulate the non-dominant cerebral hemisphere greater than the dominant cerebral hemisphere. In this embodiment differences in tone, volume and the type of auditory signal are varied to achieve the desired effect.

In operation, a sound source, such as those found on a pair of headphones, is positioned in a patient's head and the output from the headphones is directed solely to the ear associated with, or connected to, the non-dominant cerebral hemisphere. Alternatively, the sound source may be, for example, an individual speaker that is hooked on to the ear, or is held by a strap or headset. In yet another embodiment, the sound source 44 may be attached to the surface 11. In practice both ears are actually stimulated. One ear is associated with an ear piece that would play some sort of stimulating noise. Where as the opposite ear would only be stimulated from the normal sounds of the environment. The non-dominant hemisphere is related to the ear receiving extra stimulation from an auditory device.

The volume and type of sound produced by the sound source positioned over the ear to be targeted may be controlled by the user, or by an operator via a remote connection. The type of sound may be any of a range of types of musical selections, varying from classical to jazz to the use of binomial sounds and beats. Alternatively, sounds that are not human generated may be used, such as those found in nature. Examples of sounds found in nature include, but are not limited to, ocean surf, falling rain, forest sounds and the like.

The volume and type of sound generated by the sound source over the target ear may also be varied. The sound generated by the sound source stimulates the auditory pathways to the non-dominant hemispheres of the brain. The volume may be set at a constant level throughout the treatment, or, may be varied during the treatment according to the individual patient's needs and diagnosis. As with the apparatus connected to the patient's eyes, the sound sources may be self powered, or may derive their sound and power from an independent source.

In another embodiment of the present invention, the visual and auditory stimuli to the non-dominant hemisphere may be used separately but in a serial manner. Alternatively, they may be actuated concurrently, depending on the patient's individual needs.

The present invention provides a solution to the problems of individuals that have to deal with distractions on a daily basis. These distractions take away from their optimal mental health. The present invention permits individuals with internal or external distractions to focus their mental performance and their ability to perceive information. Performance and the ability to perceive and retain information is critical to those with learning disabilities, or with a need for enhanced learning abilities. The present invention is inexpensive, thereby helping those who have financial and educational needs to afford a device that selectively increases learning potential.

The ability to focus is also critical to those in the academic, business or athletic world. Using the device of the present invention, the visual and/or auditory neurological pathways of the non-dominant cortical hemisphere of individuals can be stimulated to cause excitatory post synaptic potentials (EPSP). Selectively stimulating the non-dominant cortical hemisphere to cause collateral synaptic activity of the visual and/or neurological pathways helps to achieve the goals of optimal mental health, to focus performance and to focus the person's ability to perceive and retain information.

While the visual and auditory stimulation apparatus have been described separately, one of skill in the art will know that devices may be used concurrently. When you currently use two devices may be part of a single unit and, therefore, may share the processor 41 and power source 42. Alternatively, the devices may be separate and derive their power from the same source, or from independent power sources 42.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A portable, self-contained apparatus for selectively stimulating a non-dominant cerebral hemisphere of a patient comprising:
    a surface placed in close proximity to a patient's eye;
    a plurality of lights disposed on said surface; and
    a microprocessor integrally housed in said apparatus and electrically connected to said lights and controlling said lights;
    wherein said plurality of lights selectively stimulates said patient's eye neurologically connected to said non-dominant cerebral hemisphere at a greater intensity than the dominant cerebral hemisphere and further wherein said self-contained apparatus allows said patient to roam geographically during treatment with said apparatus or to obtain treatment with said apparatus at any desired location.

2. The apparatus as recited in claim 1 further comprising a sound source for providing sound to the ear connected to said non-dominant cerebral hemishere.

3. The aparatus as recited in claim 1 wherein said surface is a pair of sunglasses or optical glasses.

4. The apparatus in claim 1 wherein the light produced by said plurality of lights is white.

5. The apparatus as recited in claim 1 wherein the light produced by said plurality of lights is plane polarized.

6. The apparatus as recited in claim 1 wherein the light produced by said plurality of lights is varied in color.

7. The apparatus as recited in according to claim 2 wherein said sound source is part of a headset.

8. A portable, self-contained apparatus for treating learning disorders by selectively stimulating a non-dominant cerebral hemisphere of a patient comprising:
    a surface placed in close proximity to a patient's eye;
    a plurality of lights disposed on said surface;
    a microprocessor integrally housed in said apparatus and electrically connected to said lights and controlling said lights, said plurality of lights being selectively controlled by said microprocessor, to allow only the lights in front of said patient's eye neurologically connected to said patient's non-dominant cerebral hemisphere to be activated; and
    a power source integrally housed in said apparatus and electrically connected to said microprocessor to provide electricity to said plurality of lights and said microprocessor.

9. The apparatus as recited in claim 8 further comprising:
    a sound source for providing sound to the ear connected to said non-dominant cerebral hemishere.

10. The apparatus as recited in claim 8 wherein said surface is a pair of sunglasses.

11. The apparatus as recited in according to claim 8 wherein the light produced by said plurality of lights is white.

12. The apparatus as recited in claim 8 wherein the light produced by said plurality of lights is plane polarized.

13. The Apparatus as recited in claim 8 wherein the light produced by said plurality of lights is varied in color.

14. The apparatus as recited in claim 11 wherein said sound source is part of a headset.

15. A method for selectively stimulating a non-dominant cerebral hemisphere of a patient comprising the steps of:
    identifying said non-dominant hemisphere of said patient;
    providing a portable, self-contained apparatus, the apparatus further comprising a surface placed in close proximity to a patient's eye; a plurality of lights disposed on said surface; a microprocessor integrally housed in said apparatus and electrically connected to said lights and controlling said lights; and
    selectively stimulating the non-dominant visual cortex and fronto-orbital cortex of said patient using said apparatus.

16. The method of claim 15 further comprising the steps of stimulating the ear connected to said non-dominant cerebral hemishere of a patient.

17. A method of claim 15 wherein said light is defined as being white light.

18. A method of claim 15 wherein said light is place polarized.

* * * * *